United States Patent
Ueno et al.

(10) Patent No.: US 8,262,225 B2
(45) Date of Patent: Sep. 11, 2012

(54) EYE EXAMINATION APPARATUS, METHOD FOR MANUFACTURING SPECTACLE LENS, SPECTACLE LENS, METHOD FOR MANUFACTURING MULTIFOCAL EYEGLASSES, AND MULTIFOCAL EYEGLASSES

(75) Inventors: Yasunori Ueno, Tokyo (JP); Kenichi Takahashi, Tokyo (JP); Norikazu Hamanaka, Tokyo (JP)

(73) Assignee: Right Mfg. Co., Ltd., Tokyo (JP)

( * ) Notice: Subject to any disclaimer, the term of this patent is extended or adjusted under 35 U.S.C. 154(b) by 8 days.

(21) Appl. No.: 13/018,541

(22) Filed: Feb. 1, 2011

(65) Prior Publication Data

US 2011/0187996 A1     Aug. 4, 2011

(30) Foreign Application Priority Data

Feb. 3, 2010 (JP) ................................ 2010-022584

(51) Int. Cl.
    *A61B 3/02*     (2006.01)
    *A61B 3/00*     (2006.01)
(52) U.S. Cl. ........................................ 351/239; 351/246
(58) Field of Classification Search ................... 351/200, 351/211, 239, 246, 168, 177
See application file for complete search history.

(56) References Cited

U.S. PATENT DOCUMENTS

| | | | |
|---|---|---|---|
| 7,296,892 B2 * | 11/2007 | Hanaki et al. | ................. 351/200 |
| 7,341,346 B2 | 3/2008 | Hanaki et al. | |
| 7,344,247 B2 | 3/2008 | Isogai et al. | |
| 2005/0174536 A1 | 8/2005 | Hanaki et al. | |

FOREIGN PATENT DOCUMENTS

| JP | 2001-394 | 1/2001 |
|---|---|---|
| JP | 2007-97707 | 4/2007 |

OTHER PUBLICATIONS

European Search Report issued to EP Application No. 11152960.8, mailed Jun. 8, 2011.

* cited by examiner

*Primary Examiner* — Jack Dinh
(74) *Attorney, Agent, or Firm* — Dilworth & Barrese, LLP.

(57) ABSTRACT

An eye examination apparatus includes an accommodation power acquisition unit, a corrected accommodation power calculation unit, a drive unit and an accommodative microfluctuation measurement unit. The accommodation power acquisition unit acquires an accommodation power which is determined from a difference between a near point and a distant point of an examined eye. The corrected accommodation power calculation unit calculates an integrated value of the accommodation power and a correction coefficient. The drive unit drives a vision target in a direction of an optical axis of the examined eye. The accommodative microfluctuation measurement unit controls the drive unit to cause the vision target to be arranged onto a corrected accommodation position corresponding to the integrated value, such that the accommodative microfluctuation measurement unit measures an eye accommodation function based on a frequency of appearance of a high frequency component representative of ciliary body accommodative microfluctuation.

16 Claims, 10 Drawing Sheets

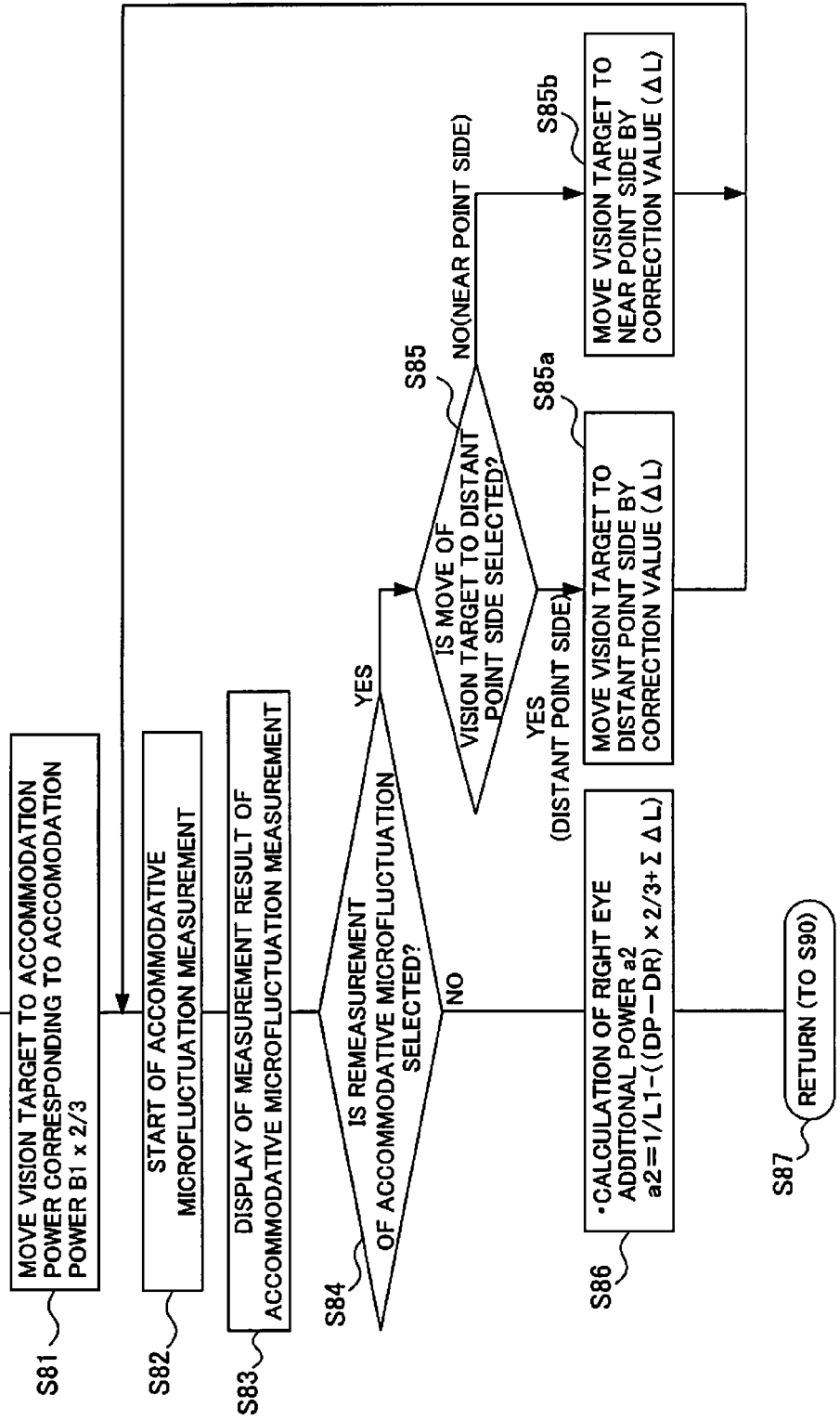

FIG. 7A

```
INITIAL SETTING
 ·NEAR USE DISTANCE L1                    :0. 3m(3. 3Dp)
 ·VERTEX DISTANCE d                       :0. 012m
 ·ROTATION CENTER DISTANCE t              :0. 013m
 ·CORRECTED DISTANCE ΔL                   :0. 25Dp

MEASUREMENT RESULT
 ·RIGHT EYE DISTANT USE DEGREE NUMBER DR  :1Dp
 ·RIGHT EYE NEAR USE DEGREE NUMBER DP     :2. 5Dp
 ·ACCOMMODATION POWER                     :1. 5Dp
 ·ADDITIONAL POWER a1                     :1. 8Dp

·APPEARANCE RATIO OF HIGH FREQUENCY
   COMPONENT                              :75%       — 19a
```

FIG. 7B

```
INITIAL SETTING
 ·NEAR USE DISTANCE L1                    :0. 3m(3. 3Dp)
 ·VERTEX DISTANCE d                       :0. 012m
 ·ROTATION CENTER DISTANCE t              :0. 013m
 ·CORRECTED DISTANCE ΔL                   :0. 25Dp

MEASUREMENT RESULT
 ·RIGHT EYE DISTANT USE DEGREE NUMBER DR  :1Dp
 ·RIGHT EYE NEAR USE DEGREE NUMBER DP     :2. 5Dp
 ·ACCOMMODATION POWER                     :1. 5Dp
 ·ADDITIONAL POWER a1                     :1. 8Dp

·APPEARANCE RATIO OF HIGH FREQUENCY
   COMPONENT                              :60%       — 19b
```

FIG. 7C

```
INITIAL SETTING
 ·NEAR USE DISTANCE L1                    :0. 3m(3. 3Dp)
 ·VERTEX DISTANCE d                       :0. 012m
 ·ROTATION CENTER DISTANCE t              :0. 013m
 ·CORRECTED DISTANCE ΔL                   :0. 25Dp

MEASUREMENT RESULT
 ·RIGHT EYE DISTANT USE DEGREE NUMBER DR  :1Dp
 ·RIGHT EYE NEAR USE DEGREE NUMBER DP     :2. 5Dp
 ·ACCOMMODATION POWER                     :1. 5Dp
 ·ADDITIONAL POWER a1                     :1. 8Dp

·APPEARANCE RATIO OF HIGH FREQUENCY
   COMPONENT                              :45%       — 19c
```

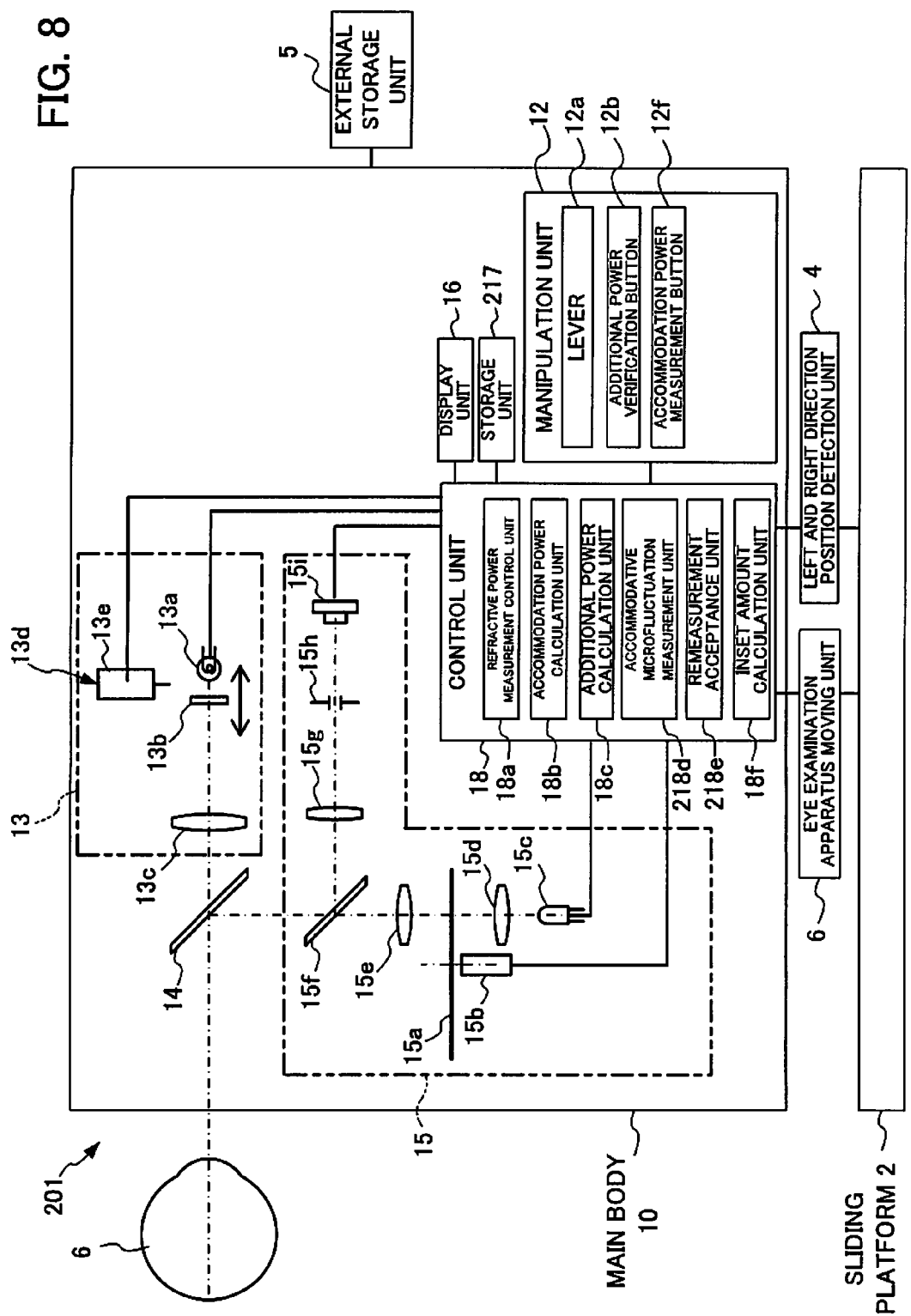

EYE EXAMINATION APPARATUS, METHOD FOR MANUFACTURING SPECTACLE LENS, SPECTACLE LENS, METHOD FOR MANUFACTURING MULTIFOCAL EYEGLASSES, AND MULTIFOCAL EYEGLASSES

This application is based on and claims the benefit of priority from Japanese Patent Application No. 2010-022584, filed on 3 Feb. 2010, the content of which is incorporated herein by reference.

BACKGROUND OF THE INVENTION

1. Field of the Invention

The present invention relates to an eye examination apparatus suitable for manufacturing multifocal eyeglasses, a method for manufacturing a spectacle lens, a spectacle lens, a method for manufacturing multifocal eyeglasses, and multifocal eyeglasses.

2. Related Art

Conventionally, there have been eye examination apparatuses that measure a distant vision refractive power and a near vision refractive power of an examined eye by moving a fixed vision table (see for example, Japanese Unexamined Patent Application Publication 2001-000394). Moreover, the accommodation power and the additional power are calculated based on the measured distant vision refractive power and the near vision refractive power, and multifocal eyeglasses (spectacles for presbyopia) have been manufactured based on this additional power.

However, conventionally, there were cases where the calculated additional power was not appropriate. In such cases, when the manufactured multifocal eyeglasses were used in a near vision distance, the examined eye sometimes experienced a tense state to suffer from tiredness.

SUMMARY OF THE INVENTION

An object of the present invention is to provide an eye examination apparatus that obtains appropriate additional power of an examined eye, a method for manufacturing a spectacle lens, a spectacle lens, a method for manufacturing multifocal eyeglasses, and multifocal eyeglasses.

The present invention achieves the object by the following means. It should be noted that, for ease of understanding, the present invention will be described using reference numerals corresponding to embodiments of the present invention, but they are not limited to them. In addition, the structure described using the reference numerals may be improved as appropriate, and at least a part of which may be substituted with other components.

In an aspect of the present invention, an eye examination apparatus is provided, which includes an accommodation power acquisition unit, a corrected accommodation power calculation unit, a drive unit and an accommodative microfluctuation measurement unit. The accommodation power acquisition unit is configured to acquire an accommodation power which is determined from a difference between a near point and a distant point of an examined eye. The corrected accommodation power calculation unit is configured to calculate an integrated value of the accommodation power acquired by the accommodation power acquisition unit and a correction coefficient. The drive unit is configured to drive a vision target in a direction of an optical axis of the examined eye. The accommodative microfluctuation measurement unit is configured to control the drive unit to cause the vision target to be arranged onto a corrected accommodation position corresponding to the integrated value calculated by the corrected accommodation power calculation unit, such that the accommodative microfluctuation measurement unit measures an eye accommodation function based on a frequency of appearance of a high frequency component representative of ciliary body accommodative microfluctuation.

In another aspect of the present invention, a method for manufacturing eyeglass lenses is provided, which includes: (a) acquiring an accommodation power that is determined from a difference between a near point and a distant point of an examined eye; (b) calculating an integrated value of the accommodation power acquired in (a) and a correction coefficient; (c) placing a vision target to a corrected accommodation position corresponding to the integrated value calculated in (b) and measuring an accommodative microfluctuation of an eye accommodation function based on a frequency of appearance of a high frequency component representative of ciliary body accommodative microfluctuation; (d) analyzing a result of the accommodative microfluctuation measurement in (c) and determining whether the examined eye is in a tense state, a proper state, or a relaxed state; (e) performing a remeasurement of accommodative microfluctuation in which the vision target is corrected to lie on a side of the distant point from the corrected accommodation position if it is determined that the examined eye is in a tense state in (d), and performing a remeasurement of accommodative microfluctuation in which the vision target is corrected to lie on a side of the near point from the corrected accommodation position if it is determined that the examined eye is in a relaxed state in (d); (f) analyzing a result of the remeasurement obtained in (e) and repeating (d) and (e) until the examined eye is determined to be in a proper state; (g) calculating an additional power based on a position of the vision target determined to be in a proper state in (d); (h) calculating an inset amount based on a refractive power of the distant point measured in (a); and (i) arranging a near vision center of a near vision refraction portion of a lens of multifocal eyeglasses corresponding to the additional power calculated in (g) based on the inset amount calculated in (h).

In another aspect of the present invention, a method for manufacturing multifocal eyeglasses is presented which includes: (a) acquiring an accommodation power that is determined from a difference between a near point and a distant point of an examined eye; (b) calculating an integrated value of the accommodation power acquired in (a) and a correction coefficient; (c) placing a vision target to a corrected accommodation position corresponding to the integrated value calculated in (b) and measuring an accommodative microfluctuation of an eye accommodation function based on a frequency of appearance of a high frequency component representative of ciliary body accommodative microfluctuation; (d) analyzing a result of the accommodative microfluctuation measurement in (c) and determining whether the examined eye is in a tense state, a proper state, or a relaxed state; (e) performing a remeasurement of accommodative microfluctuation in which the vision target is corrected to lie on a side of the distant point from the corrected accommodation position if it is determined that the examined eye is in a tense state in (d), and performing a remeasurement of accommodative microfluctuation in which the vision target is corrected to lie on a side of the near point from the corrected accommodation position if it is determined that the examined eye is in a relaxed state in (d); (f) analyzing a result of the remeasurement obtained in (e) and repeating (d) and (e) until the examined eye is determined to be in a proper state; (g) calculating an additional power based on a position of the vision target determined to be in a proper state in (d); (h) calculating an inset amount based on a refractive power of the distant point measured in (a); and (i) arranging a near vision center of a near vision refraction portion of a lens of multifocal eyeglasses corresponding to the additional power calculated in (g) based on the inset amount calculated in (h).

According to the present invention, there are following advantageous effects.

(1) Since the present invention arranges the vision target to the corrected accommodation position and measures the eye accommodation function based on the ciliary body accommodative microfluctuation, it is possible to determine whether the corrected accommodation position, that is, the additional power, is suitable.

(2) Since the present invention accepts the remeasurement of the accommodative microfluctuation in which the vision target is corrected to lie on the side of the distant point from the corrected accommodation position, when it is determined that the additional power is not appropriate, the examiner can obtain an appropriate additional power by remeasuring the accommodative microfluctuation.

(3) Since the present invention accepts the remeasurement of the accommodative microfluctuation in which the vision target is corrected to lie on the side of the near point from the corrected accommodation position, when it is determined that there is an allowance in the accommodation power, the examiner can obtain an appropriate additional power by remeasuring the accommodative microfluctuation measurement.

(4) Since the present invention repeatedly accepts the remeasurement of the accommodative microfluctuation, the examiner can obtain the additional power with great precision.

(5) Since the present invention remeasures the accommodative microfluctuation in which the vision target is corrected to lie on the side of the distant point from the corrected accommodation position when it is determined that the examined eye is in a tense state, it is possible to obtain advantageous effects similar to above (2) by determining whether the eye examination apparatus remeasures automatically.

(6) Since the present invention remeasures the accommodative microfluctuation measurement in which the vision target is corrected to lie on the side of the near point from the corrected accommodation position when it is determined that there is an allowance in the accommodation power, it is possible to obtain advantageous effects similar to above (3) by determining whether the eye examination apparatus remeasures automatically.

(7) Since the present invention repeats the remeasurement of the accommodative microfluctuation according to the determination result performed by the measurement result determination unit, it is possible to obtain advantageous effects similar to above (4) by determining whether the eye examination apparatus remeasures automatically.

(8) Since the present invention determines the state of the examined eye by selecting the determination criterion based on the manipulation through the manipulation unit, it is possible to determine the state of the examined eye in consideration of the individual differences such as examinee's age.

(9) Since the present invention includes the additional power calculation unit for calculating the additional power based on the position of the vision target that is driven according to the measurement performed by the accommodative microfluctuation measurement unit, it is possible to obtain appropriate additional power after confirming that the examined eye is not in a tense state by the accommodative microfluctuation measurement unit.

(10) Since the objective refractive power measurement unit measures the distant point refractive power (distant vision refractive power) and the near point refractive power (near vision refractive power) of the examined eye in the present invention, it is possible to measure the accommodation power appropriately in consideration of the accommodative microfluctuation using so-called auto refractometer.

(11) Since the present invention includes the inset amount calculation unit, when manufacturing a lens of multifocal eyeglasses, it is possible to obtain the position of the near vision center of the refraction unit of the lens for near vision by a series of processing of calculating the inset amount from the objective refractive power measurement.

(12) Since the present invention includes the selection unit for selecting whether to perform the inset amount calculation or the accommodative microfluctuation measurement, the examiner can confirm whether the additional power is appropriate by the accommodative microfluctuation measurement before calculating the inset amount.

(13) The present invention calculates the additional power based on the position of the vision target that is determined to be in a proper state in the measurement result determination; calculates the inset amount based on the distant point refractive power measured in the accommodation power acquisition; and sets the near vision center of the near vision refraction portion in the lens of multifocal eyeglasses based on the additional power and calculated inset amount. In this manner it is possible to measure the accommodation power and make the optical axis setting of the near vision refraction portion as a continuous series from the determination of whether the additional power that uses the accommodation power is suitable. As a result, it is possible to simplify the multifocal spectacle lens and the manufacture of eyeglasses and to manufacture a lens and eyeglasses suitable for the examinee.

BRIEF DESCRIPTION OF THE DRAWINGS

FIG. 6 is a flow chart showing an operation of right eye additional power verification processing according to the first embodiment;

FIGS. 7A-7C are views showing examples of the display on the display unit 16 according to the first embodiment;

FIG. 8 is a block diagram of an eye examination apparatus 201 according to a second embodiment;

DETAILED DESCRIPTION OF THE INVENTION

First Embodiment

Hereafter, embodiments of the present invention will be described with reference to the drawings.

Figure 1:
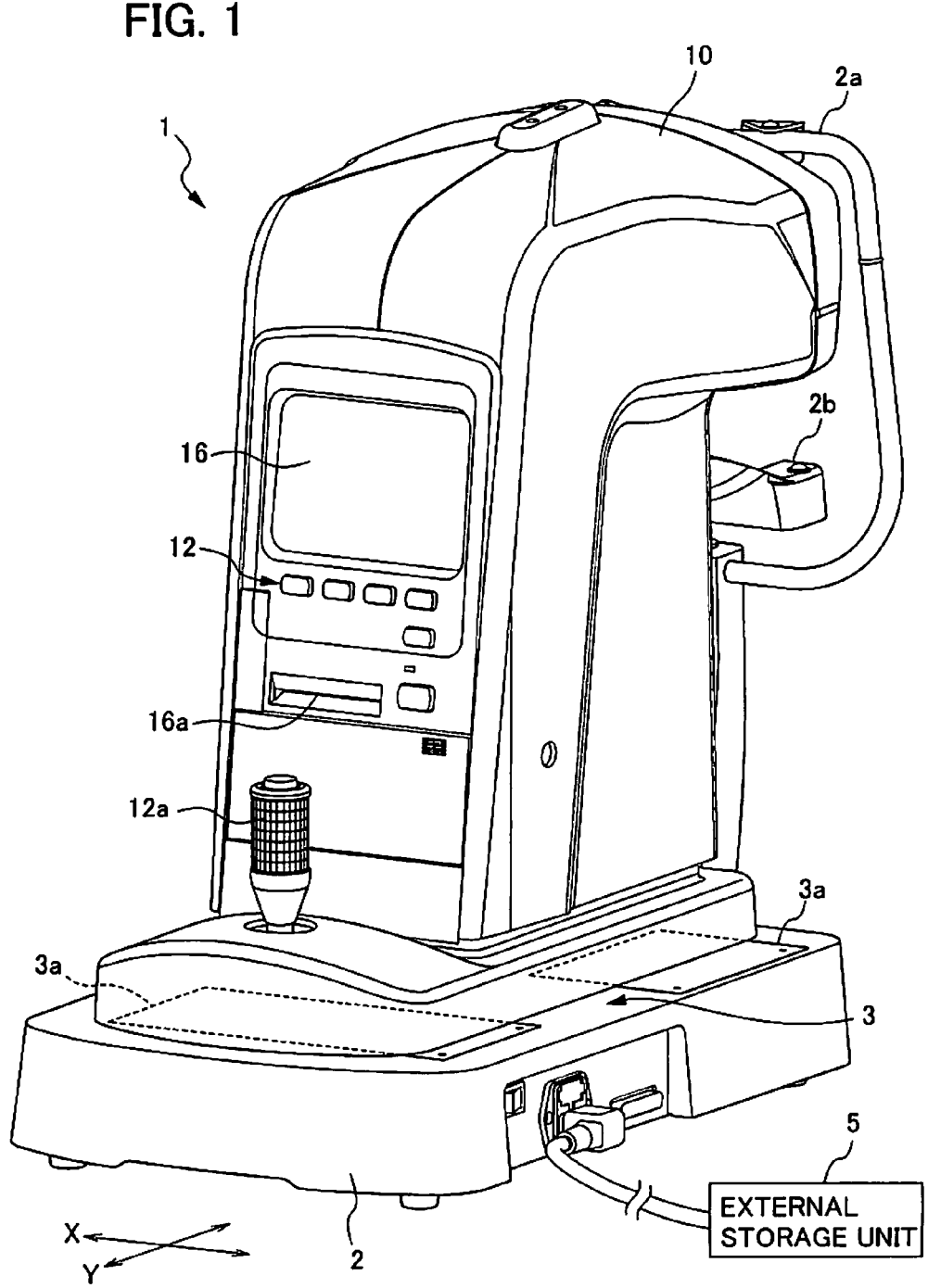
FIG. 1 is an external view of an eye examination apparatus 1 according to a first embodiment.

FIG. 1 is an external view of an eye examination apparatus 1 according to the first embodiment.

Figure 2:
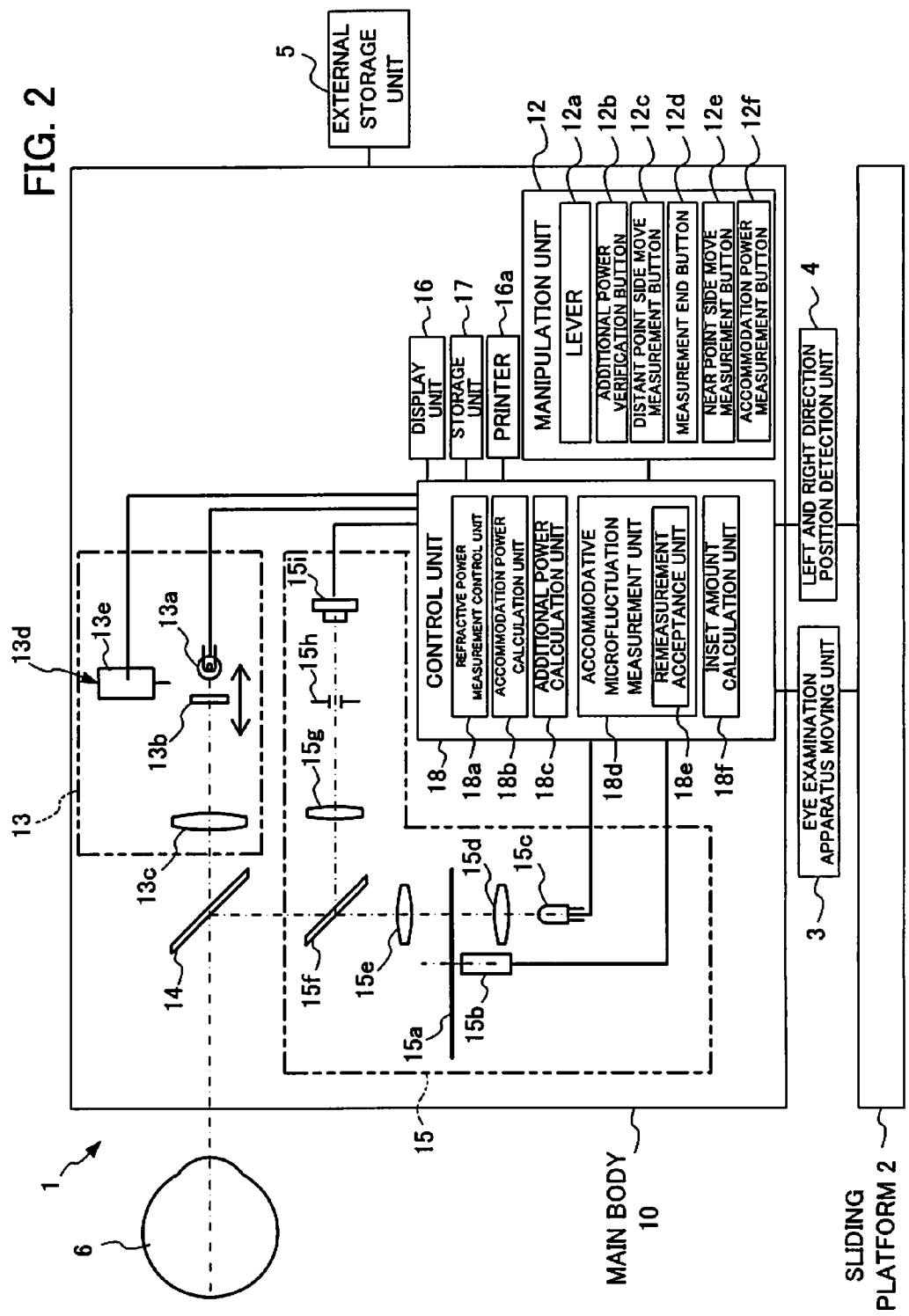
FIG. 2 is a block diagram of the eye examination apparatus 1 according to the first embodiment.

FIG. 2 is a block diagram of the eye examination apparatus 1 according to the first embodiment.

Figure 3:
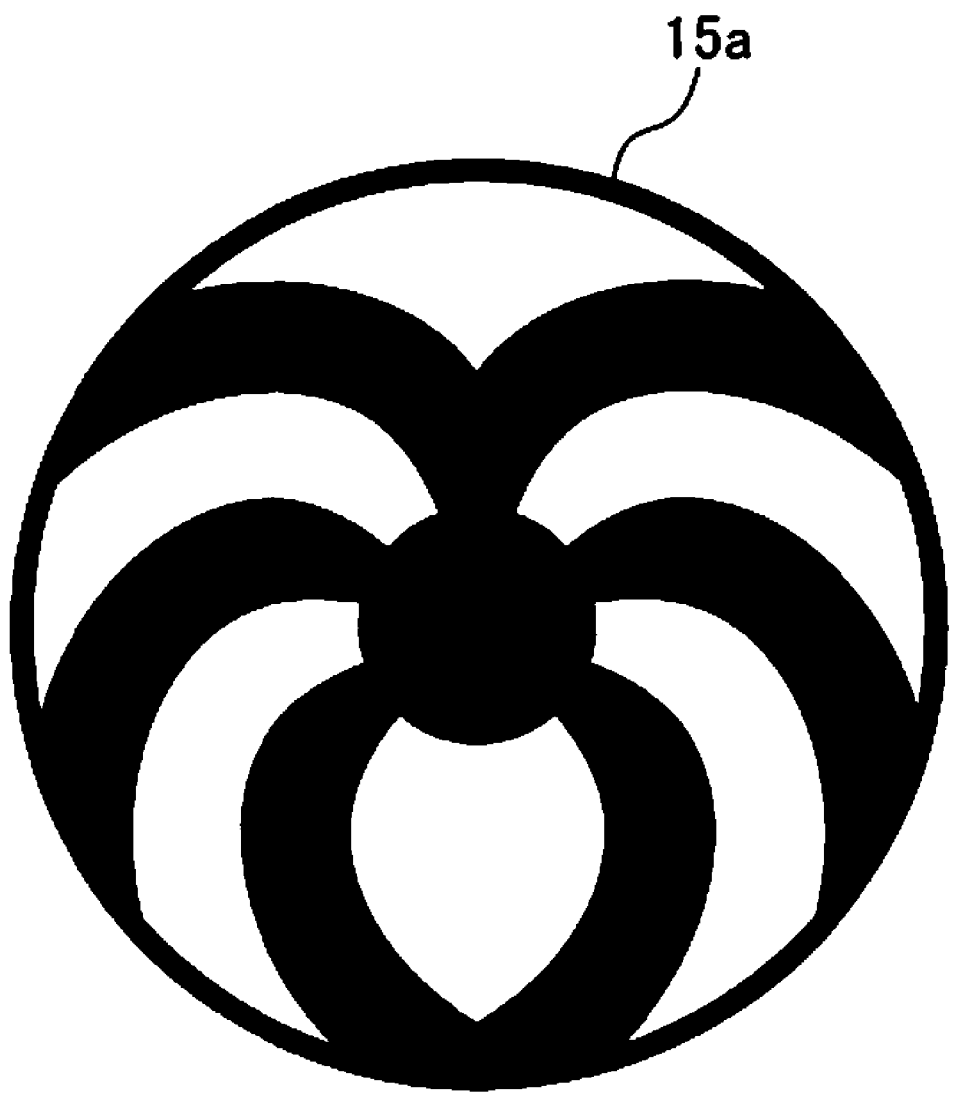
FIG. 3 is a view showing a striped pattern of a chopper 15a according to the first embodiment.

FIG. 3 is a view showing a striped pattern of a chopper 15a according to the first embodiment.

Figure 4:
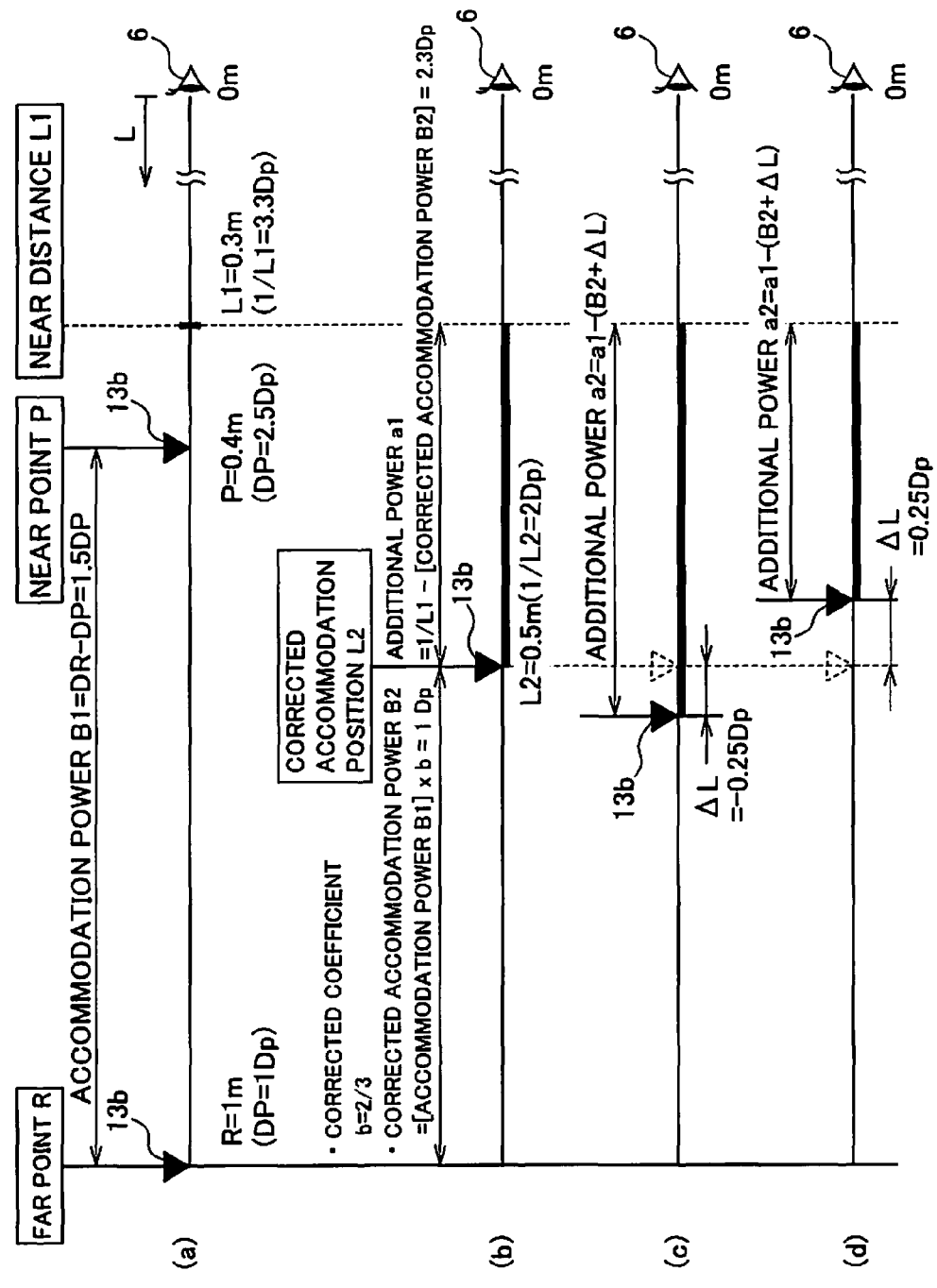
FIG. 4 is a view illustrating an example of the measurement at a distant point R and a near point P and an example of the measurement of accommodative microfluctuation according to the first embodiment.

FIG. 4 is a view illustrating an example of the measurement at a distant point R and a near point P according to the first embodiment, and an example of the measurement of the accommodative microfluctuation.

As shown in FIG. 1 and FIG. 2, the eye examination apparatus 1 includes a sliding platform 2, an eye examination apparatus moving unit 3, a left and right direction position detection unit 4, and a main body 10.

The sliding platform 2 serves as a base for the eye examination apparatus 1, and is set at the time of measurement on a desk or the like. The sliding platform 2 is provided with a forehead contact 2a, a jaw receiving portion 2b, and the like, which fix the face of an examinee at the time of measurement.

The eye examination apparatus moving unit 3 supports the main body 10 movable to a left and right direction X and a back and forth direction Y with respect to the sliding platform 2. The eye examination apparatus moving unit 3 includes a slider mechanism 3a, a DC motor (not illustrated) that drives the main body 10 to the left and right direction X and the back and forth direction Y, and the like. The eye examination apparatus moving unit 3 is controlled by a control unit 18 according to the manipulation of a lever 12a.

The left and right direction position detection unit 4 is a photo sensor and the like which detect a position of the main body 10 with respect to the sliding platform 2. The left and right direction position detection unit 4 outputs a detection signal to the control unit 18.

In addition, the eye examination apparatus 1 includes an external memory unit 5 for data storage.

The main body 10 is provided with main parts of the eye examination apparatus 1. The main body 10 is movable in the left and right direction X and the back and forth direction Y with respect to the sliding platform 2 by the manipulation of the lever 12a according to the position of an examined eye 6 of the examinee, which is fixed to the face receiving portion 2a.

The main body 10 includes a manipulation unit 12, a target projection unit 13, an eye refractive power measurement apparatus 15 (objective refractive power measurement unit), a dichroic mirror 14, a display unit 16 (output unit), a storage unit 17, and the control unit 18 and the like.

The manipulation unit 12 is an input unit for an examiner (measuring personnel) to manipulate this eye examination apparatus 1, and is provided at a case of the eye examination apparatus 1. The manipulation unit 12 has buttons or the like, through which initial values and various manipulations are inputted. The manipulation unit 12 includes the lever 12a, an additional power verification button 12b, a distant point side move measurement button 12c, a measurement end button 12d, a near point side move measurement button 12e, and an accommodation power measurement button 12f.

The lever 12a is for moving the vision target projection unit 13 and the eye refractive power measurement apparatus 15 to the left and right direction X and the back and forth direction Y together.

The additional power verification button 12b is a button to be operated in order to select whether verification processing of the right eye additional power is performed, after calculating an additional power a1 of the right eye as described later. The additional power verification button 12b is similarly operated in order to select whether to perform verification processing of the left eye additional power, after calculating an additional power a1 of the left eye.

The distant point side move measurement button 12c is a manipulation button for measuring accommodative microfluctuation again by moving the vision target 13b toward the distant point R in the right eye additional power verification processing (described later).

The measurement end button 12d is a manipulation button for ending the measurement of the accommodative microfluctuation measurement.

The near point side move measurement button 12e is a manipulation button for measuring the accommodative microfluctuation measurement again by moving the vision target 13b toward the near point P in the right eye additional power verification processing (described later).

The accommodation power measurement button 12f is a button for measuring the distant vision refractive power of the right eye by moving the vision target 13b toward the distant point R, and further measuring the near vision refractive power of the right eye by moving it toward the near point P.

The distant point side move measurement button 12c, the near point side move measurement button 12e, and the accommodation power measurement button 12f are similarly operated for the left eye.

The vision target projection unit 13 allows the vision target 13b to be observed by the examined eye 6. Sequentially from a side far from the examined eye 6, the vision target projection unit 13 includes a light source 13a, a vision target 13b, and a convex lens 13c, and the drive unit 13d.

The light source 13a illuminates the vision target 13b.

The vision target 13b is a component observed by the examined eye 6.

The convex lens 13c transforms rays of light from the vision target 13b into substantially parallel luminous flux and introduces it into the examined eye 6. Accordingly, the vision target 13b is observed by the examined eye 6 as if it were farther than the actual position.

The drive unit 13d moves the light source 13a and the vision target 13b in an optical axis direction. The drive unit 13d is controlled by the control unit 18. The drive unit 13d includes a slider mechanism (not illustrated), a motor 13e, and a rotary encoder (not illustrated).

The slider mechanism supports the light source 13a and the vision target 13b movable in the optical axis direction while the positional relationship between them is maintained unchanged.

The motor 13e is a DC motor or the like, which moves the light source 13a and the vision target 13b.

The rotary encoder detects a position of the vision target 13b in the optical axis direction, and is an optical encoder, for example. The rotary encoder is attached to a revolving shaft of the motor 13e. The rotary encoder outputs a detection signal to the control unit 18.

The dichroic mirror 14 guides the measuring light (infrared light) emitted from the eye refractive power measurement apparatus 15 and the observation light (visible light) emitted from the vision target projection unit 13 to the examined eye 6, respectively. In addition, the dichroic mirror 14 causes the infrared light returning back from the examined eye 6 to be back to the eye refractive power measurement apparatus 15.

The eye refractive power measurement apparatus 15 includes a chopper 15a, a motor 15b, a light source 15c (infrared light source), lenses 15d and 15e, a half mirror 15f, a lens 15g, an aperture 15h, and a light receiving portion 15i.

The chopper 15a is disc-shaped and rotatable.

As shown in FIG. 3, slits that project a striped pattern on the fundus of the examined eye 6 are formed at the chopper 15a. At the striped pattern, stripes in two kinds of directions are formed, and when the chopper 15a goes around one time, the two meridian directions are measured to calculate the eye refractive power (described later).

As shown in FIG. 2, the motor 15b rotates the chopper 15a.

The light source 15c is an infrared light source that illuminates the chopper 15a.

The lenses 15d and 15e are lenses that project the striped pattern formed by the infrared light of the light source 15c and the chopper 15a on the fundus of the examined eye 6.

The half mirror 15f guides the infrared light returned from the fundus of the examined eye 6 to the light receiving portion 15i.

The lens 15g, the aperture 15h, and the light receiving portion 15i are detection units for detecting the migration velocity of the striped pattern formed by the infrared light returned from the fundus of the examined eye 6.

The light receiving portion 15i is a photo detection device that receives light returned from the fundus of the eye. The light receiving portion 15i outputs the received light signal to the control unit 18.

The eye refractive power measurement apparatus 15 rotates the chopper 15a to move the striped pattern projected on the fundus of the examined eye 6. At this time, the migration velocity of the striped pattern formed on the light receiving portion 15i changes according to the eye refractive power of the examined eye 6. Thereby, as described above, when the chopper 15a goes around one time, the eye refractive power is calculated.

This eye refractive power is distant vision refractive power (distant point refractive power) DR and near vision refractive power (near point refractive power) DP. The eye refractive power measurement apparatus 15 calculates data of spherical refractive power (S), astigmatism refractive power (C), and astigmatism axis (AX), respectively. When calculating an accommodation power generally, the distant vision equivalent spherical refractive power and the near vision equivalent spherical refractive power are calculated respectively to obtain the accommodation power using: equivalent spherical refractive power=S+C/2.

Hereafter, for easier understanding, the equivalent spherical refractive power is simply referred to as "refractive power" without considering the astigmatism refractive power.

The display unit 16 is a display unit that outputs various measurement results of eye refractive power, interpupillary distance (pupil distance) and accommodative microfluctuation, the visual image of the examined eye 6, the calculation result of an inset amount i, and the like. The display unit 16 is a liquid crystal display, for example, and is provided so that the examiner can observe. It should be noted that according to the output of the manipulation unit 12, the control unit 18 prints on paper the contents outputted to the display unit 16 by controlling the printer 16a.

The storage unit 17 is a storage device such as a hard disk, a semiconductor memory device and the like for storing a program, information and the like required for the operation of the eye examination apparatus 1.

The control unit 18 controls the overall eye examination apparatus 1 and is composed of CPU (central processing unit), for example. The control unit 18 works together with the hardware described above by reading various programs stored in the storage unit 17 as appropriate and executing them to realize various functions related to the present invention.

The control unit 18 drives the vision target projection unit 13 and the eye refractive power measurement apparatus 15 based on the output of the detection units or the manipulation unit 12, performs the measurements, and stores and reads data in the storage unit 17, for example.

The control unit 18 includes a refractive power measurement control unit 18a, an accommodation power calculation unit 18b (an accommodation power acquisition unit, a corrected accommodation power calculation unit), an additional power calculation unit 18c, an accommodative microfluctuation measurement unit 18d, and an inset amount calculation unit 18f, and communicates information between these control units if needed.

The refractive power measurement control unit 18a measures the eye refractive power of the distant vision and the near vision of the examined eye 6. The refractive power measurement control unit 18a controls the vision target projection unit 13 and the refractive power measurement apparatus 15 based on the output of the detection units or the manipulation unit 12, measures the distant vision refractive power DR and the near vision refractive power DP of the examined eye 6, and calculates the distant point R and the near point P.

In a measurement example shown in (a) of FIG. 4, a result of measurement of the examined eye 6 indicates:

$$\text{distant point } R = 1\text{m}$$

$$\text{distant vision refractive power } DR = 1/R = 1/1\text{m} = 1Dp$$

Similarly, if near point P=0.4 m:

$$\text{near vision refractive power } DP = 1/0.4\text{m} = 2.5Dp$$

The accommodation power calculation unit 18b acquires accommodation power B1 and corrected accommodation power B2 which are determined from the difference between a near point P and a distant point R of the examined eye 6.

In the example of the measurement in FIG. 4:

$$\text{accommodation power } B1 = DP - DR = 1.5Dp \qquad \text{Formula (1)}$$

The accommodation power calculation unit 18b calculates the corrected accommodation power B2 (integrated value) by integrating the accommodation power B1 and a correction coefficient b acquired by the accommodation power calculation unit 18b.

It should be noted that the reason for correcting the accommodation power B1 to the corrected accommodation power B2 in this way is that when eyeglasses for use in a near vision distance L1 are manufactured based on the near point P, the accommodation power is fully consumed when seeing near vision at the time of use in the near vision distance L1, forcing the examined eye 6 to experience an unnatural state (tense state). It should be noted that the near vision distance L1 is a distance based on which eyeglasses are manufactured and at which the examinee uses the eyeglasses. For example, the examinee actually places a book etc. to be spaced apart at such a distance when she or he uses the eyeglasses for reading.

In the example of the measurement in FIG. 4: correction coefficient b=⅔, and $$\text{corrected accommodation power } B2 = \text{accommodation power } B1 \times \text{correction coefficient } b = 1.5Dp \times 2/3 = 1Dp \qquad \text{Formula (2)}$$

The additional power calculation unit 18c calculates an additional power a1 based on corrected accommodation power B2 and a near vision distance L1.

Additional power is a term used in a prescription of a multifocal lens for presbyopias and indicates a difference between the distant vision refractive power and the near vision refractive power, and in general becomes stronger if the near vision distance L is shorter and stronger if the accommodation power is lower.

In the example of the measurement in FIG. 4: near vision distance L1=0.3 m, and $$\text{additional power } a1 = 1/(\text{near vision distance } L1) - \text{corrected accommodation power } B2 = 1/0.3 - 1 \approx 2.3 Dp \quad \text{Formula (3)}$$

It should be noted that, as described later, when the vision target 13b is moved by additional power verification processing, the additional power calculation unit 18c calculates additional power a2 based on the position of the vision target 13b that is moved in the measurement performed by the accommodative microfluctuation measurement unit 18d.

The accommodative microfluctuation measurement unit 18d measures accommodative microfluctuation (eye accommodation function) based on the frequency of appearance of the high frequency component that shows ciliary body accommodative microfluctuation. The accommodative microfluctuation measurement unit 18d performs accommodative microfluctuation measurement in a state where the vision target 13b has been arranged at a corrected accommodation position L2 that corresponds to the corrected accommodation power B2, or remeasures the accommodative microfluctuation based on the output from the remeasurement acceptance unit 18e.

A method described in Japanese Patent No. 4173296 is used for the measurement of the accommodation function. Explaining briefly, time-dependent change data of the refractive power acquired at a certain target position is subjected to Fourier-transformation by FFT (fast Fourier transform), for example, such that the ciliary body accommodative microfluctuation is analyzed. An examiner can determine whether the examined eye 6 is in a tense state, a proper state, or a relaxed state based on a frequency of appearance of high frequencies 1 to 2.3 Hz that indicate that the examined eye 6 is in the tense state.

The examiner can determine as follows based on the frequency of appearance of the high frequencies 1 to 2.3 Hz:

The frequency of appearance is 70% or more: tense state

The frequency of appearance is greater than or equal to 50% and less than 70%: proper state The frequency of appearance is less than 50%: relaxed state (state having sufficient allowances in the additional power)

The accommodative microfluctuation measurement unit 18d includes the remeasurement acceptance unit 18e.

The remeasurement acceptance unit 18e is a control unit that accepts the remeasurement of the accommodative microfluctuation after the display unit 16 outputs a measurement result. According to manipulation of the distant point side move measurement button 12c and the near point side move measurement button 12e, the remeasurement acceptance unit 18e drives the vision target 13b toward the distant point R or the near point P by an amount of the correction value ΔL (Dp) such that the position of the vision target 13b is corrected.

The inset amount calculation unit 18f calculates an inset amount i based on distant vision refractive power DR and a near vision distance L1 which are measured by the refractive power measurement control unit 18a.

The inset amount i is obtained by the following expression:

$$\text{inset amount } i = p/(1+((1/(d+t)-DR/1000))\times(L1-d)) \quad \text{Formula (4)}$$

wherein p: one eye pupil distance, d: vertex distance, t: distance of center of eyeball rotation (distance from the apex of cornea to the center of eyeball rotation)

The one eye pupil distance p means a distance from the center of the examinee's face to the pupil center of each of the right and left eyes. On the other hand, a pupil distance means a distance between the pupil centers of the right and left eyes. As described later, since the pupil distance is measurable in the present embodiment, the inset amount i is calculated based on "one eye pupil distance p=pupil distance/2."

It should be noted that when the one eye pupil distance p is measurable, the inset amount i may be calculated by using that value.

Figure 5:
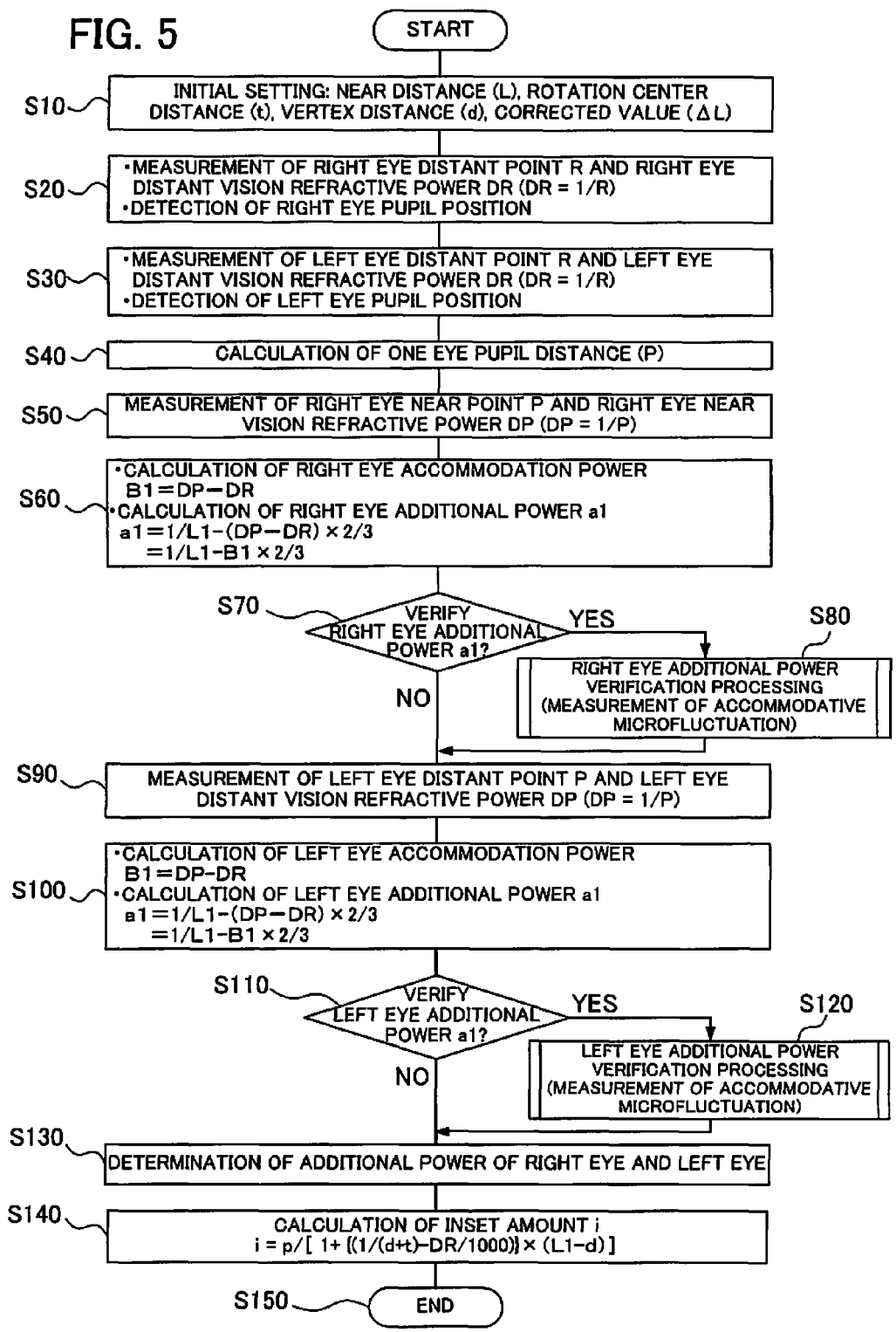
FIG. 5 is a flow chart showing an operation of the entire eye examination apparatus 1 according to the first embodiment.

FIG. 5 is a flow chart showing the operation of the entire eye examination apparatus 1 according to the first embodiment.

FIG. 6 is a flow chart showing the operation of the right eye additional power verification processing according to the first embodiment.

FIG. 7 is a view showing a display example of the display unit 16 according to the first embodiment.

It should be noted that the following description will be based on the measurement example shown in FIG. 4.

In Step S10 (hereinafter simply referred to as "S10"), when an examiner manipulates the manipulation unit 12 to input an initial value, the control unit 18 accepts the input of the initial value.

The control unit 18 accepts the input of a near vision distance L1, a vertex distance d, a distance of center of eyeball rotation t, and a correction value ΔL as the initial value.

In the example in FIG. 4, the near vision distance L1 is 0.3 m.

The value of the vertex distance d is 0.012 m if an examinee is Japanese, for example, and is 0.013 to 0.015 m if an examinee is of European decent. In addition, generally, the values of the vertex distance d and the distance of center of eyeball rotation t are set so that the addition of the vertex distance d and the distance of center of eyeball rotation t is 0.025 m if the examinee is Japanese and is 0.027 m if the examinee is of European decent.

The correction value ΔL will be described later.

In S20, when the accommodation power measurement button 12f is manipulated by the examiner, the refractive power measurement control unit 18a measures a distant vision refractive power DR of an right examined eye 6 (right eye) of the examinee.

When performing this measurement, the refractive power measurement control unit 18a controls the drive unit 13d according to the manipulation of the lever 12a, and moves the vision target projection unit 13 and the eye refractive power measurement apparatus 15, such that the optical axis of the vision target projection unit 13 and the eye refractive power measurement apparatus 15 and the optical axis of the right eye are aligned. The refractive power measurement control unit 18a stores a position of the right eye in the left and right direction X in the storage unit 17. The position of X is stored in order to measure a pupil distance PD. (This will be described later.)

Thereafter, the refractive power measurement control unit 18a moves the vision target 13b, and measures the right eye distant vision refractive power DR.

In S30, when the accommodation power measurement button 12f is manipulated by the examiner, the refractive power measurement control unit 18a measures a left eye distant vision refractive power DR of the left examined eye 6 (left eye) of the examinee.

When this measurement is performed, as in S20, the refractive power measurement control unit 18a controls the drive unit 13d according to the manipulation of the lever 12a, aligns the optical axis of the vision target projection unit 13 and the eye refractive power measurement apparatus 15 and the optical axis of the left eye, and stores a position of the left eye in the left and right direction X in the storage unit 17. Then, when the refractive power no longer shows change, the left eye distant vision refractive power DR is measured.

In S40, the control unit 18 calculates a pupil distance based on the positions of the left eye and right eye in the left and right direction X, which have been stored in the storage unit 17.

In S50, when the accommodation power measurement button 12f is manipulated by the examiner, the refractive power measurement control unit 18a measures a right eye near vision refractive power DP.

When this measurement is performed, the refractive power measurement control unit 18a accepts the manipulation of the lever 12a first, and aligns the optical axis of the vision target projection unit 13 and the eye refractive power measurement apparatus 15 and the optical axis of the right eye. The refractive power measurement control unit 18a controls the drive unit 13d and moves the vision target 13b in the direction of the right eye. When the refractive power no longer shows change, it measures the right eye near vision refractive power DP.

In S60, the accommodation power calculation unit 18b calculates accommodation power B1 based on the right eye distant vision refractive power DR and the right eye near vision refractive power DP according to Formula (1) (acquisition of the accommodation power). In addition, the accommodation power calculation unit 18b calculates right eye additional power a1 based on the accommodation power B1 and a correction coefficient b (=2/3) according to Formula (2) and Formula (3) (calculation of the corrected accommodation power).

In S70, the control unit 18 determines whether or not the verification of the right eye additional power a1 is selected, according to the manipulation of the manipulation unit 12 by the examiner. If it is determined that the verification of the right eye additional power a1 is selected (S70: YES), the control unit 18 proceeds to S80 and performs the verification processing of the right eye additional power a1. If it is determined that the verification of the right eye additional power a1 is not selected (S70: NO), the control unit 18 proceeds to S90.

Right Eye Additional Power Verification Processing

The right eye additional power verification processing shown in FIG. 6 will be described.

As shown in (b) of FIG. 4, in the verification processing of the right eye additional power a1, the accommodative microfluctuation measurement unit 18d initially causes the vision target 13b to move to the corrected accommodation value L2 corresponding to the corrected accommodation power B2 (1 Dp) in S81.

In S82, the accommodative microfluctuation measurement unit 18d starts the accommodative microfluctuation measurement.

By the above processing in S81 and S82, the accommodative microfluctuation measurement unit 18d moves the vision target 13b to the corrected accommodation position L2, and measures the eye accommodation function (accommodative microfluctuation measurement).

In S83, the accommodative microfluctuation measurement unit 18d outputs a result of the accommodative microfluctuation measurement onto the display unit 16.

As shown in FIG. 7A, since an appearance ratio is greater than or equal to 75% when a frequency of appearance of the high frequency component is 75% (refer to column 19a), for example, it can be determined that the right eye is in a tense state when the vision target 13b lies at the corrected accommodation position L2. In this case, the examiner can select the remeasurement of the accommodative microfluctuation described later by manipulating the distant point side move measurement button 12c.

As shown in FIG. 7B, when a frequency of appearance is 60%, for example, which is greater than or equal to 50% and less than 70% (refer to column 19b), the examiner can determine that the right eye is in a proper state for a case where the vision target 13b is at the corrected accommodation position L2. In this case, the examiner need only to manipulate the measurement end button 12d, and need not select the remeasurement of accommodative microfluctuation.

As shown in FIG. 7C, when the frequency of appearance is 45%, for example, which is less than 50% (refer to column 19c), the examiner can determined that the right eye is in a relaxed state for a case where the vision target 13b is at the corrected accommodation position L2. In this case, the examiner can select the remeasurement of the accommodative microfluctuation described later by manipulating the near point side move measurement button 12e.

In S84, based on the output of the manipulation unit 12, the remeasurement acceptance unit 18e accepts the selection of whether to remeasure the accommodative microfluctuation. As described above, based on the result of the accommodative microfluctuation measurement, the examiner can select whether to remeasure the accommodative microfluctuation by manipulating the distant point side move measurement button 12c or the near point side move measurement button 12e. When the remeasurement of the accommodative microfluctuation is selected (S84: YES), the remeasurement acceptance unit 18e proceeds to S85. Alternatively, when the remeasurement of the accommodative microfluctuation is not selected, it proceeds to S86 (S84: NO).

When the result of the accommodative microfluctuation measurement is a tense state, as shown in (c) of FIG. 4, the examiner may move the vision target 13b toward the distant point R in the direction in which the right eye changes from a tense state to a proper state.

On the other hand, when the result of the accommodative microfluctuation measurement is a relaxed state, as shown in (d) of FIG. 4, the examiner may move the vision target 13b toward the near point P in the direction in which the right eye changes from a relaxed state to a proper state.

In S85, the remeasurement acceptance unit 18e determines which of the distant point side move measurement button 12c or the near point side move measurement button 12e has been selected in S84.

When it is determined that the distant point side move measurement button 12c is manipulated, the remeasurement acceptance unit 18e proceeds to S85a (S85: YES) and on the other hand, when it is determined that the near point side move measurement button 12e is manipulated, it proceeds to S85b (S85: NO).

In S85a, the remeasurement acceptance unit 18e drives the vision target 13b toward the distant point R by an amount of the correction value ΔL (minus) (refer to (c) of FIG. 4), and thereafter, the accommodative microfluctuation measurement unit 18d repeats the processing from S82. Regarding the correction value ΔL, a minus sign is assigned to the correction toward the distant point R and a plus sign is assigned to the correction toward the near point P with respect to the corrected accommodation value L2. Accordingly, when the vision target 13b is moved toward the distant point R by |ΔL|, the sign is minus, and when the vision target 13b is moved toward the near point P by |ΔL|, the sign is plus.

The correction value ΔL, which is expressed as a Diopter unit, can be selected like movement per 0.125 Dp, movement per 0.25 Dp, and so on (S10). The correction value ΔL of 0.25 Dp is assumed in the present description.

On the other hand, in S85b, the remeasurement acceptance unit 18e repeats the processing from S82 by driving the vision target 13b toward the near point P by the correction value ΔL (refer to FIG. 4(d)). It should be noted that when the vision target 13b is moved toward the near point P, the direction of movement is opposite from the case when it is moved toward the distant point R.

In the repeated processing starting from S82, the accommodative microfluctuation measurement unit 18d remeasures accommodative microfluctuation (remeasurement) by moving the position of the vision target 13b toward the distant point R by the correction value ΔL (minus) or toward the near point P side by the correction value ΔL, and displays a result of the measurement.

In this manner, it is possible for the examiner to repeat a remeasurement of the accommodative microfluctuation until the appearance ratio of the high frequency component fall in an appropriate range of values greater than or equal to 50% and less than 70% (remeasurement repetition measurement).

In S86, the additional power calculation unit 18c calculates an additional power a2 based on the position of the vision target 13b driven during the remeasurement performed by the accommodative microfluctuation unit 18d (additional power calculation). That is, the additional power a2 is expressed by a mathematical formula:

$$\text{additional power } a2 = 1/L1 - ((DP-DR) \times \tfrac{2}{3} + \Sigma \Delta L)$$

Here, the correction value ΔL has a minus sign when the vision target 13b is driven toward the distant point R and a plus sign when it is driven toward the near point P.

In the example (c) of FIG. 4, ΣΔL=−0.5 Dp when the vision target 13b moves toward the distant point R by the correction value ΔL (−0.25 Dp) two times. Accordingly, the following formula holds good:

$$\text{additional power } a2 = 1/0.3 - ((2.5-1) \times \tfrac{2}{3} - 0.5) = 2.8 Dp$$

It should be noted that when the remeasurement of the accommodative microfluctuation is not selected even for one time, that is, when the flow has not passed through "S84: YES", the additional power calculation unit 18c rewrites the additional power a1 calculated in S60 as additional power a2=additional power a1.

Thereafter, the control unit 18 proceeds to S90 (S87).

Returning to FIG. 5, in S90-S120, the control unit 18 performs processing for the left eye similar to the processing for the right eye S50-S80 and calculates the additional power a1, a2 of the left eye.

In S130, the additional power calculation unit 18c determines the additional power a for both the left eye and the right eye.

When the right eye additional power a1 has not been verified (S70: NO), the additional power calculation unit 18c determines: right eye additional power a=a1 (calculated in S60), and on the other hand, when the right eye additional power a1 has been verified (S70: YES): right eye additional power a=a2 (calculated in S80 (S86)).

Similarly, when the left eye additional power a1 has not been verified (S110: NO), it decides: left eye additional power a=a1 (calculated in S100), and on the other hand, when the left eye additional power a1 has been verified (S110: YES), it decides: right eye additional power a=a2 (calculated in S120).

In S140, the inset amount calculation unit 18f calculates an inset amount i according to Formula (4) based on the refractive power that is measured by the refractive power measurement control unit 18a (inset amount calculation). The inset amount calculation unit 18f outputs the calculated inset amount i onto the display unit 16. Thereafter, the control unit 18 ends a series of processing (S150).

It should be noted that in the above-described processing, the examiner may not measure the accommodative microfluctuation such that the inset amount i is directly calculated without the accommodative microfluctuation measurement. In such a case, the examiner may manipulate the manipulation unit 12 (selection unit) so that additional power verification processing is not selected, in S70 and S110. In this manner, the examiner can confirm whether the additional power is proper if the accommodative microfluctuation measurement is selectively performed.

As explained above, the eye examination apparatus 1 of the present embodiment determines whether the calculated additional power a is proper.

Accordingly, when the additional power a is corrected from a tense state to a proper state, it is possible to manufacture multifocal eyeglasses that do not cause the examined eye 6 to be tired when the multifocal eyeglasses are used at a near vision distance L1.

On the other hand, when the additional power a is corrected from a relaxed state to a proper state, it is possible to allow the additional power a to be small. Accordingly, it is possible to manufacture multifocal eyeglasses that have small bumps and distortion in the lens.

Second Embodiment

Next, a second embodiment of an eye examination apparatus in accordance with the present invention will be described.

It should be noted that in the following explanation and the drawings, the same reference label or the reference label with the same postfix is assigned to the part that serves the same function with the above first embodiment, and the overlapped description is omitted as appropriate.

FIG. 8 is a block diagram of an eye examination apparatus 201 according to the second embodiment.

The eye examination apparatus 201 includes a storage unit 217 and a measurement result determination unit 218g.

The storage unit 217 stores the following determination criterion that is similar to that of the first embodiment:

the frequency of appearance is greater than or equal to 70%: tense state the frequency of appearance is greater than or equal to 50% and less than 70%: proper state the frequency of appearance is less than 50%: relaxed state The measurement result determination unit 218g analyzes a measurement result obtained by the accommodative microfluctuation measurement unit 218d, and determines whether an examined eye 6 is in a tense state, a relaxed state, and a proper state in accordance with the determination criterion stored in the storage unit 217 based on a frequency of appearance of high frequencies 1 to 2.3 Hz.

That is, the examiner determines the state of the examined eye 6 in the first embodiment, whereas the eye examination apparatus 201 determines by itself a state of the examined eye 6 in the second embodiment.

Figure 9:
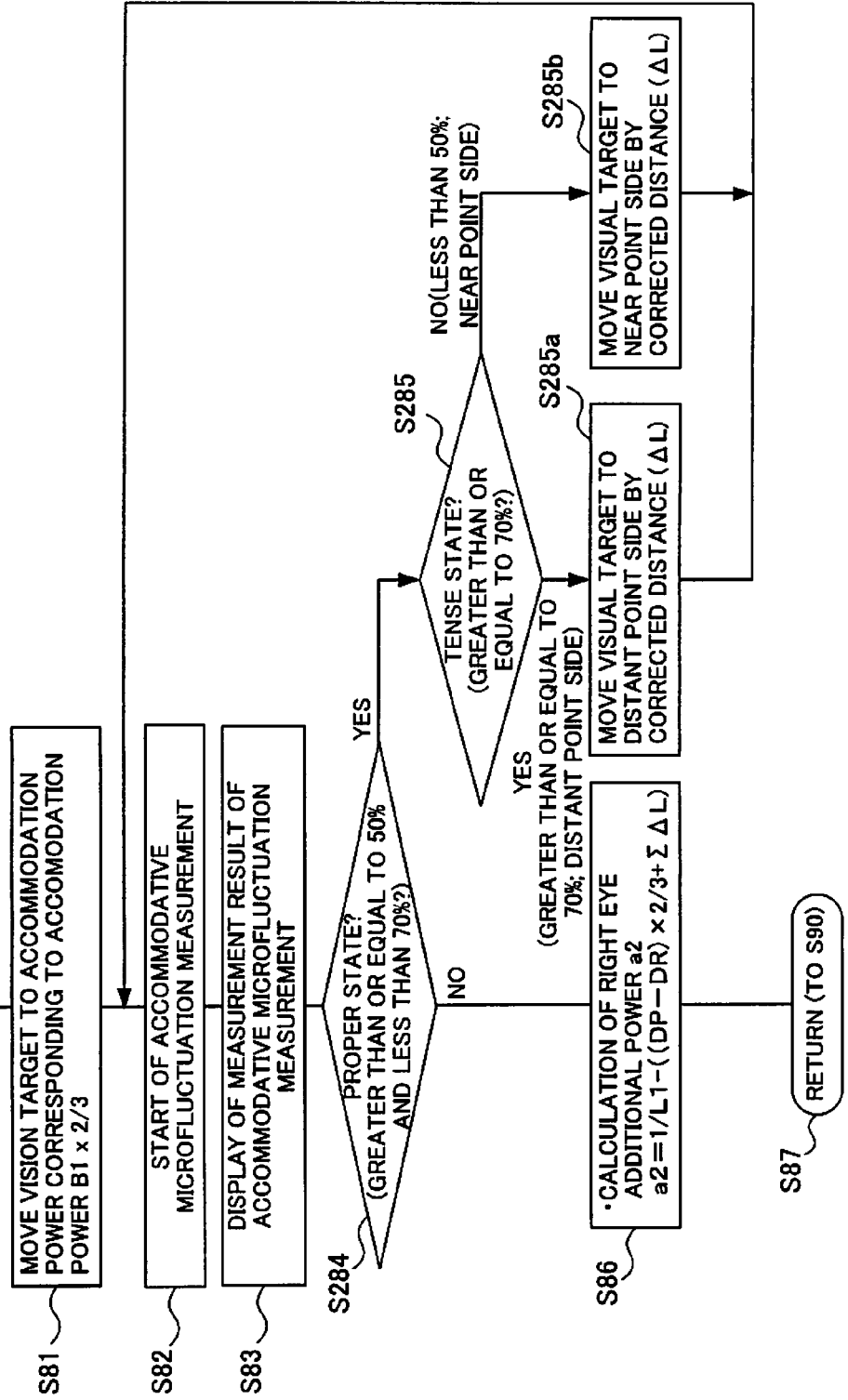
FIG. 9 is a flow chart showing an operation of right eye additional power verification processing according to the second embodiment.

FIG. 9 is a flow chart showing the operation of right eye additional power verification processing according to the second embodiment.

In S284, the measurement result determination unit 218g analyzes a result obtained by the accommodative microfluctuation measurement unit 218d, and determines whether the examined eye 6 is in a proper state. When the measurement result determination unit 218g determines that the examined eye 6 is in a proper state (S284: YES), it proceeds to S285, and on the other hand, when it determines that the examined eye 6 is not in a proper state (S284: NO), it proceeds to S86.

The processing in S86 is similar to that of the first embodiment, and the additional power calculation unit 18c calculates an additional power a2.

In S285, the measurement result determination unit 218g determines whether the examined eye 6 is in a tense state or in a relaxed state. When the measurement result determination unit 218g determines that the examined eye 6 is in a tense state (S285: YES), it proceeds to S285a, and contrary, when it determines that the examined eye 6 is not in a tense state, that is, in a relaxed state (S285: NO), it proceeds to S285b.

In S285a, similarly to the first embodiment, the accommodative microfluctuation measurement unit 218d drives the vision target 13b toward the distant point R by an amount of the correction value ΔL (Dp) and repeats the processing starting from S82.

In S285b, similarly to the first embodiment, the accommodative microfluctuation measurement unit 218d drives the vision target 13b toward the near point P by an amount of the correction value ΔL (Dp), and repeats the processing starting from S82.

As explained above, the eye examination apparatus 201 determines by itself the state of the examined eye 6 and calculates an appropriate additional power a.

Third Embodiment

Next, a third embodiment of the present invention will be described.

The third embodiment is directed to a method for manufacturing multifocal eyeglasses 350 and a multifocal lens 360 (spectacle lens) using the eye examination apparatus 1 according to the first embodiment.

Figure 10:
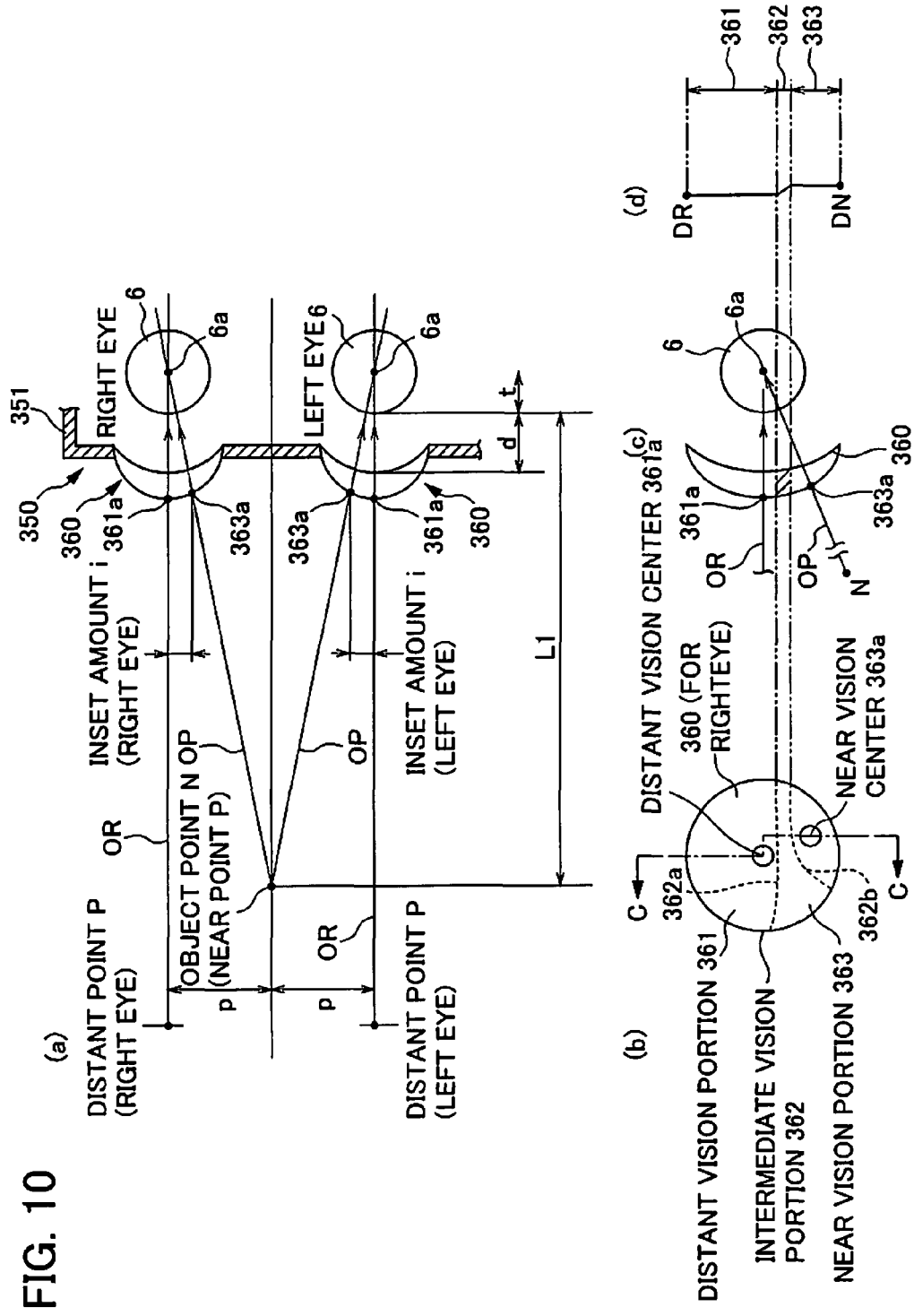
FIGS. 10A-10B are views illustrating methods for manufacturing multifocal eyeglasses 350 and the multifocal lens 360 according to a third embodiment.

FIG. 10 is a view illustrating the method for manufacturing the multifocal eyeglasses 350 and the multifocal lens 360 according to the third embodiment.

Diagram (a) of FIG. 10 is a top view of an examinee wearing the multifocal eyeglasses 350.

Diagram (b) of FIG. 10 is a front view of a right eye multifocal lens 360 (viewed from a side of a far point P).

Diagram (c) of FIG. 10 is a side view of the positional relationship between the right eye multifocal lens 360 and the examined eye 6 while an examinee is wearing the multifocal eyeglasses 350 (from the lower side in (a) of FIG. 10 (cross-sectional view taken along c-c in (b) of FIG. 10). It is a view for illustrating the examinee seeing continuously from the distant to the near while moving the line of vision up and down with the eyeball rotating about the center of eyeball rotation 6a.

Diagram (d) of FIG. 10 is a graph illustrating the change in the refractive power of the multifocal lens 360.

As shown in (a) of FIG. 10, left and right multifocal lenses 360 are fixed onto a frame 351 in the multifocal eyeglasses 350.

As shown in (b) of FIG. 10, the multifocal lens 360 includes a distant vision portion 361 (distant vision refraction portion), an intermediate vision portion 362, and a near vision portion 363 (near vision refraction portion). The multifocal lens 360 is a progressive multifocal lens among the lenses that enables one to see from the distant to the near with one lens.

This progressive multifocal lens is a lens in which a boundary line 362a of the distant vision portion 361 and the intermediate vision portion 362 and a boundary line 362b of the intermediate vision portion 362 and the near vision portion 363 are not visually observable. It should be noted that (b) of FIG. 10 shows the boundary lines 362a and 362b with broken lines in order to express the boundaries of the distant vision portion 361, the intermediate vision portion 362, and the near vision portion 363.

The distant vision portion 361 is a portion for distant vision of the upper side of the multifocal lens 360 and its refractive power DR is constant (refer to (d) of FIG. 10).

The intermediate vision portion 362 is a portion between the distant vision portion 361 and the near vision portion 363. Its refractive power changes from the refractive power DR to the refractive power DN continuously as a position moves from the upper side of the lens to the lower side (refer to (d) of FIG. 10).

The near vision portion 363 is a portion for near vision of the lower side of the multifocal lens 360 and its refractive power DN is constant (refer to (d) of FIG. 10). In the multifocal lens, the additional power is (DN-DR).

The method for manufacturing the multifocal eyeglasses 350 will be described now.

The multifocal eyeglasses 350 are manufactured according to the following sequence. It should be noted that the following processes may be a work of optical design performed on a drawing or the like, for example, in order to manufacture the multifocal eyeglasses 350.

(1) First, an examiner obtains a distant vision refractive power DR, a near vision refractive power DN, an additional power a2, an inset amount i, and the like of right and left examined eyes 6 of an examinee by performing processing in FIG. 5 and FIG. 6 according to the first embodiment. Among these values, the distant vision refractive power DR, the additional power a2, and the inset amount i are needed for the prescription of the eyeglasses.

(2) As shown in (a) of FIG. 10, two multifocal lenses 360 for the right eye and the left eye (examined eye 6) are arranged onto a frame 351 (lens arrangement).

(3) The examiner arranges a distant vision portion 361 on each multifocal lens 360 (distant vision portion arrangement).

In this process, the examiner arranges a distant vision center 361a so that each distant vision optical axis OR, which reaches a center of eyeball rotation 6a of each of the right eye and the left eye when the examined eye 6 sees an infinite point, passes through a distant vision center 361a (center of the distant vision portion 361 in terms of optical design).

It should be noted that the examiner sets the distant vision refractive power DR obtained in the process (1) as the refractive power of the distant vision portion 361.

(4) The examiner arranges the near vision portion 363 on each multifocal lens 360 (near vision portion arrangement).

In this process, the examiner arranges a near vision center 363a so that each near vision optical axis OP, which reaches the center of eyeball rotation 6a when the examined eye 6 sees an object point N, passes through the near vision center 363a (center of the near vision portion 363 in terms of optical design) (near vision center arrangement).

It should be noted that when the examinee observes the object point N at a near vision distance L1, the eyeball rotates to the inside. For this reason, the examiner arranges the near vision center 363a by shifting by the inset amount i obtained in the above processing to the inside with respect to each distant vision optical axis OR, so that each near vision optical axis OP runs aslant by passing through the near vision center 363a.

It should be noted that the examiner sets the near vision refractive power DN obtained in the process (1) as each refractive power of the near vision portion 363.

(5) The examiner arranges the intermediate vision portion 362 onto each multifocal lens 360 (intermediate vision portion arrangement).

At this process, the examiner arranges the intermediate vision portion 362 between the distant vision portion 361 and the near vision portion 363 arranged at the above process. The examiner sets a shape of a lens for the intermediate vision portion 362 so that the refractive power changes continuously from the refractive power DR to the refractive power DN.

As explained above, the method for manufacturing the multifocal eyeglasses 350 and the multifocal lens 360 of the present embodiment performs the process from measurement of the examined eye 6 to the design of the multifocal lens 360 by a series of processes using the eye examination apparatus 1 according to the first embodiment. In addition, since the distant vision refractive power DR, the near vision refractive power DN, the additional power a2, and the inset amount i are measured, an optical design is performed using the distant vision refractive power DR, the additional power a2, and the inset amount i among these values. In this manner, it is possible not only to allow the process for manufacturing the multifocal eyeglasses 350 to be simple, but also to manufacture the multifocal eyeglasses 350 optimal for individuals (examinees) who need to wear eyeglasses.

It should be noted that although an example that uses the eye examination apparatus 1 according to the first embodiment has been described in this embodiment, even if the eye examination apparatus 201 according to the second embodiment is used, it is possible to manufacture the multifocal eyeglasses 350 and the multifocal lens 360 similarly.

Although embodiments of the present invention have been described above, the present invention should not be limited to the above embodiments, and various modification and changes are possible as in the modified forms described later and they are also within the technical scope of the present invention. In addition, the advantageous effects described in the embodiments are merely the result of enumerating the most suitable advantageous effects that arise from the present invention, and the advantageous effects of the present invention are not limited to what is described in the embodiments. It should be noted that the above embodiments and the modified forms described later may be combined suitably to be used but the detailed description thereof is omitted.

Modified Embodiment

Although one example for the determination criterion stored in the storage unit is shown in the second embodiment, it is not limited to this. For example, a plurality of determination criteria may be stored in the storage unit in the form of a table according to the age of an examinee and the like, and the measurement result determination unit may select the determination criterion according to the manipulation of the manipulation unit. Thereby, it is possible to determine the state of an examined eye in consideration of individual differences, such as the age of the examinee.

What is claimed is:

1. An eye examination apparatus comprising:
  an accommodation power acquisition unit configured to acquire an accommodation power which is determined from a difference between a near point and a distant point of an examined eye;
  a corrected accommodation power calculation unit configured to calculate an integrated value of the accommodation power acquired by the accommodation power acquisition unit and a correction coefficient;
  a drive unit configured to drive a vision target in a direction of an optical axis of the examined eye; and
  an accommodative microfluctuation measurement unit configured to control the drive unit to cause the vision target to be arranged onto a corrected accommodation position corresponding to the integrated value calculated by the corrected accommodation power calculation unit, such that the accommodative microfluctuation measurement unit measures an eye accommodation function based on a frequency of appearance of a high frequency component representative of ciliary body accommodative microfluctuation.

2. The eye examination apparatus according to claim 1 further comprising an output unit configured to output a measurement result obtained by the accommodative microfluctuation measurement unit, wherein
  the accommodative microfluctuation measurement unit includes a remeasurement acceptance unit configured to accept a remeasurement of accommodative microfluctuation in which the vision target is corrected to lie on a side of the distant point from the corrected accommodation position after outputting of the measurement result performed by the output unit.

3. The eye examination apparatus according to claim 1 further comprising an output unit configured to output a measurement result obtained by the accommodative microfluctuation measurement unit, wherein
  the accommodative microfluctuation measurement unit includes a remeasurement acceptance unit configured to accept a remeasurement of accommodative microfluctuation in which the vision target is corrected to lie on a side of one of the distant point and the near point from the corrected accommodation position after outputting of the measurement result performed by the output unit.

4. The eye examination apparatus according to claim 3 wherein
  the output unit outputs the remeasurement of the accommodative microfluctuation performed by the accommodative microfluctuation measurement unit, and
  the remeasurement acceptance unit repeatedly accepts a remeasurement of the accommodative microfluctuation in which a position of the vision target in the remeasurement is corrected to lie on the side of one of the distant point and the near point.

5. The eye examination apparatus according to claim 1 further comprising
  a measurement result determination unit configured to determine whether the examined eye is in a tense state by analyzing a measurement result of the accommodative microfluctuation measurement unit, wherein
  in a case in which the examined eye is determined to be in a tense state by the measurement result determination unit, the accommodative microfluctuation measurement unit performs a remeasurement of accommodative microfluctuation in which the vision target is corrected to lie on a side of the distant point from the corrected accommodation position.

6. The eye examination apparatus according to claim 1 further comprising:
a measurement result determination unit configured to determine whether the examined eye is in one of a tense state and a relaxed state by analyzing a measurement result of the accommodative microfluctuation measurement unit, wherein
in a case in which the examined eye is determined to be in the tense state by the measurement result determination unit, the accommodative microfluctuation measurement unit performs a remeasurement of accommodative microfluctuation in which the vision target is corrected to lie on a side of the distant point from the corrected accommodation position, and
in a case in which the examined eye is determined to be in the relaxed state by the measurement result determination unit, the accommodative microfluctuation measurement unit performs a remeasurement of accommodative microfluctuation in which the vision target is corrected to lie on a side of the near point from the corrected accommodation position.

7. The eye examination apparatus according to claim 6 wherein
the measurement result determination unit determines a state of the examined eye by analyzing the measurement result of the remeasurement performed by the accommodative microfluctuation measurement unit, and
the accommodative microfluctuation measurement unit repeats a remeasurement of the accommodative microfluctuation in which a position of the vision target in the remeasurement of the accommodative microfluctuation is corrected to lie on a side of one of the distant point and the near point according to a determination result of the measurement result determination unit.

8. The eye examination apparatus according to claim 7 further comprising:
a storage unit configured to store a plurality of determination criteria; and
a manipulation unit configured to accept selection by an examiner, wherein
the measurement result determination unit selects an determination criterion stored in the storage unit based on manipulation through the manipulation unit and determines the state of the examined eye based on the selected determination criterion.

9. The eye examination apparatus according to claim 1 further comprising
an additional power calculation unit configured to calculate an additional power based on a position of the vision target driven according to a measurement performed by the accommodative microfluctuation measurement unit.

10. The eye examination apparatus according to claim 1 wherein
the accommodation power acquisition unit includes an objective refractive power measurement unit configured to measure a refractive power of the distant point and the near point of the examined eye.

11. The eye examination apparatus according to claim 1 further comprising
an inset amount calculation unit configured to calculate an inset amount based on a refractive power of the distant point measured by the accommodation power acquisition unit.

12. The eye examination apparatus according to claim 11 further comprising
a selection unit configured to select whether to calculate an inset amount or to measure an accommodative microfluctuation according to a measurement result obtained by the accommodative microfluctuation measurement unit.

13. A method for manufacturing eyeglass lenses comprising:
(a) acquiring an accommodation power that is determined from a difference between a near point and a distant point of an examined eye;
(b) calculating an integrated value of the accommodation power acquired in (a) and a correction coefficient;
(c) placing a vision target to a corrected accommodation position corresponding to the integrated value calculated in (b) and measuring an accommodative microfluctuation of an eye accommodation function based on a frequency of appearance of a high frequency component representative of ciliary body accommodative microfluctuation;
(d) analyzing a result of the accommodative microfluctuation measurement in (c) and determining whether the examined eye is in a tense state, a proper state, or a relaxed state;
(e) performing a remeasurement of accommodative microfluctuation in which the vision target is corrected to lie on a side of the distant point from the corrected accommodation position if it is determined that the examined eye is in a tense state in (d), and performing a remeasurement of accommodative microfluctuation in which the vision target is corrected to lie on a side of the near point from the corrected accommodation position if it is determined that the examined eye is in a relaxed state in (d);
(f) analyzing a result of the remeasurement obtained in (e) and repeating (d) and (e) until the examined eye is determined to be in a proper state;
(g) calculating an additional power based on a position of the vision target determined to be in a proper state in (d);
(h) calculating an inset amount based on a refractive power of the distant point measured in (a); and
(i) arranging a near vision center of a near vision refraction portion of a lens of multifocal eyeglasses corresponding to the additional power calculated in (g) based on the inset amount calculated in (h).

14. Eyeglass lenses manufactured by the method according to claim 13.

15. A method for manufacturing multifocal eyeglasses comprising:
(a) acquiring an accommodation power that is determined from a difference between a near point and a distant point of an examined eye;
(b) calculating an integrated value of the accommodation power acquired in (a) and a correction coefficient;
(c) placing a vision target to a corrected accommodation position corresponding to the integrated value calculated in (b) and measuring an accommodative microfluctuation of an eye accommodation function based on a frequency of appearance of a high frequency component representative of ciliary body accommodative microfluctuation;
(d) analyzing a result of the accommodative microfluctuation measurement in (c) and determining whether the examined eye is in a tense state, a proper state, or a relaxed state;

(e) performing a remeasurement of accommodative microfluctuation in which the vision target is corrected to lie on a side of the distant point from the corrected accommodation position if it is determined that the examined eye is in a tense state in (d), and performing a remeasurement of accommodative microfluctuation in which the vision target is corrected to lie on a side of the near point from the corrected accommodation position if it is determined that the examined eye is in a relaxed state in (d);

(f) analyzing a result of the remeasurement obtained in (e) and repeating (d) and (e) until the examined eye is determined to be in a proper state;

(g) calculating an additional power based on a position of the vision target determined to be in a proper state in (d);

(h) calculating an inset amount based on a refractive power of the distant point measured in (a); and (i) arranging a near vision center of a near vision refraction portion of a lens of multifocal eyeglasses corresponding to the additional power calculated in (g) based on the inset amount calculated in (h).

16. Multifocal eyeglasses manufactured by the method according to claim 15.

* * * * *